United States Patent [19]

Sabol et al.

[11] 4,377,527

[45] Mar. 22, 1983

[54] AMMONIA CATALYZED PREPARATION OF ZINC DIHYDROCARBYL DITHIOPHOSPHATES

[75] Inventors: Albert R. Sabol, Munster, Ind.; Nicolas C. Petrellis, Lisle, Ill.

[73] Assignee: Standard Oil Company (Indiana), Chicago, Ill.

[21] Appl. No.: 242,107

[22] Filed: Mar. 9, 1981

[51] Int. Cl.$^3$ .............................................. C07F 3/06
[52] U.S. Cl. ............................ 260/429.9; 252/32.7 E; 260/987
[58] Field of Search ............... 252/32.7 E; 260/429.9, 260/987

[56] References Cited

U.S. PATENT DOCUMENTS

| | | | |
|---|---|---|---|
| 2,680,123 | 6/1954 | Mulvany | 252/32.7 E X |
| 2,689,220 | 9/1954 | Mulvany | 252/32.7 E |
| 2,766,207 | 10/1956 | McDermott | 252/32.7 E |
| 2,977,382 | 3/1961 | Millikan | 252/32.7 E X |
| 3,347,790 | 10/1967 | Meinhardt | 252/32.7 E X |
| 3,351,647 | 11/1967 | Butler et al. | 252/32.7 E X |
| 3,361,856 | 1/1968 | LeSuer | 252/32.7 E X |
| 3,554,908 | 1/1971 | Dickert, Jr. et al. | 252/32.7 E |
| 4,104,291 | 8/1978 | Sabol et al. | 252/32.7 E X |
| 4,113,634 | 9/1978 | Sabol et al. | 252/32.7 E |
| 4,253,975 | 3/1981 | Law et al. | 252/32.7 E |

*Primary Examiner*—Andrew Metz
*Attorney, Agent, or Firm*—Richard A. Kretchmer; William T. McClain; William H. Magidson

[57] ABSTRACT

Ammonia compounds improve zinc dihydrocarbyl dithiophosphate compositions and processes for their preparation.

13 Claims, No Drawings

AMMONIA CATALYZED PREPARATION OF ZINC DIHYDROCARBYL DITHIOPHOSPHATES

This application relates to lubricating oil additive compositions comprising zinc salts of a dihydrocarbyl dithiophosphoric acid and to processes for their preparation. More particularly, this invention relates to a class of novel catalysts used in the neutralization reaction between a dihydrocarbyl dithiophosphoric acid and a basically reacting zinc compound, to obtain the desired degree of acid neutralization by incorporating sufficient zinc into the additive composition.

Zinc hydrocarbyl dithiophosphate additive compositions provide resistance to wear, corrosion and oxidation to internal combustion engine crankcase lubricants. The additive is commonly prepared by the neutralization reaction of a basically reacting zinc compound and a dihydrocarbyl dithiophosphoric acid which in turn can be made by reacting a phosphorus sulfide compound with a hydrocarbyl hydroxy compound. Certain disadvantages have been encountered in the neutralization reaction and with the resulting zinc additives.

The utilization of zinc compounds and the desired degree of neutralization of the acid has often been erratic. Often a large excess of zinc compound, up to 50 mole percent excess, or 1.5 mole of zinc per mole of acid, high temperatures and long reaction times, are needed to drive the neutralization reaction to completion. Substantially all of the excess zinc compound is wasted since a neutral additive composition, having a pH greater than about 6, requires about a stoichiometric amount of zinc. Elevated reaction temperatures used to drive the reaction to completion can often cause decomposition of the dithiophosphoric acid and the accumulation of decomposition byproducts in the oil. The incorporation of insufficient zinc and the thermal decomposition of the thiophosphoric acid often results in sour (pH less than 6), hazy products that fail to provide sufficient wear, oxidation and corrosion resistance to crankcase lubricants.

The erratic reactivity and purity of both the basic zinc compounds and the phosphorus sulfide compound, from which the dihydrocarbyl diphosphoric acid is produced, have been implicated in the reaction problems.

U.S. Pat. Nos. 2,983,742; 3,361,668; 3,573,293; and 3,826,745 each teach the use of amine compounds such as ethanol amines, alkyl amines, cycloalkyl amines, hydrocarbyl amines, etc. to improve the properties of zinc additives. These patents suffer from the disadvantage that they treat zinc dihydrocarbyl dithiophosphate additive compositions with a substantial proportion of relatively expensive amine compound to provide increased performance to the additive. Further, amine compounds in general have been implicated as varnish deposit precursors when present in internal combustion crankcase lubricants.

Accordingly, a need exists for improved zinc dihydrocarbyl dithiophosphate additives and for improved processes for their preparation. Preferably, the zinc additives of this invention should (1) have a pH greater than about 6, (2) be thermally stable (resistant to the generation of haze and hydrogen sulfide) and (3) provide substantial wear, oxidation and corrosion resistance to crankcase lubricants.

A primary object of the invention is to improve zinc dihydrocarbyl dithiophosphate compositions and processes for their production. Another object is to reduce the excess of zinc compound required to neutralize the acid and to reduce the severity of other reaction conditions. Another object of the invention is to increase the incorporation of zinc into the additive composition. A further object of the invention is to produce a zinc additive composition having a pH greater than about 6 which is thermally stable and maintains the corrosion resistance, wear resistance and oxidation resistance of crankcase lubricants containing the zinc additive. Still another object of the invention is to reduce waste of zinc compound in the production of the zinc additives. Further objects appear hereinafter.

We have found that the zinc additive composition of this invention, which is the neutralization reaction product of a basically reacting zinc compound and a dihydrocarbyl dithiophosphoric acid, can be improved by including in the neutralization reaction mixture a catalytic amount of an ammonia compound or an ammonia-yielding compound. By catalytic amounts of ammonia we mean less than about 10 mole percent of the stoichiometric amount of ammonia or ammonia-yielding compound required to neutralize the dihydrocarbyl dithiophosphoric acid present in the reaction mixture.

While we do not wish to be limited by a theory of action of the ammonia or ammonia-yielding compound, apparently the action of free ammonia or ammonium species in the reaction mixture maintains the reactivity of the zinc compound particles. In the presence of the ammonium or ammonia-yielding compound sufficient zinc compound rapidly reacts with and sufficiently neutralizes the dihydrocarbyl dithiophosphoric acid to incorporate substantial amounts of zinc, such that the pH of the resulting composition is greater than about 6.

Briefly, the improved lubricating oil additives of this invention can be prepared by neutralizing a dihydrocarbyl dithiophosphoric acid compound with a zinc compound in the presence of a catalytic amount of an ammonia compound or an ammonia-yielding compound.

Ammonia compounds useful as neutralization catalysts in the reaction between the zinc compound and the acid include any ammonia compound which can be the source of or which generates ammonia or ammonium species in the reaction mixture containing the zinc compound and the acid. Ammonia or ammonia-yielding compounds include those compounds which decompose or generate ammonia or ammonium species at reaction temperature. Generally useful ammonia compounds or ammonia-yielding compounds include ammonia gas, ammonium hydroxide, ammonium salts of mineral acids, ammonium salts of organic acids, etc. Specific examples include ammonium nitrate, ammonium chloride, ammonium sulfate, ammonium acetate, ammonium benzoate, ammonium hydrocarbyl sulfonate, ammonium alkylbenzene sulfonate, ammonium alkenyl sulfonate, hexamethylene tetraamine (the condensation product of about 6 moles of formaldehyde and about 4 moles of ammonia). Preferred ammonia compounds, for reasons of ease of use, low cost and availability, include gaseous ammonia, ammonium hydroxide and ammonium sulfonate.

Commonly, dihydrocarbyl dithiophosphoric acids are manufactured by reacting about 4 molar equivalents of a hydrocarbyl hydroxy compound, such as an aliphatic alcohol, or mixtures thereof with about 1 molar equivalent of a phosphorus sulfide compound at temperatures about 50°–150° C. with the accompanying evolution of hydrogen sulfide, as illustrated by the following reaction sequence:

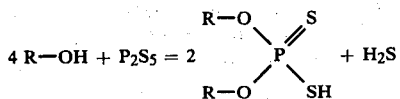

The oil soluble zinc salt is commonly manufactured by neutralizing the above acid compound with a basically reacting zinc compound, preferably zinc oxide or zinc hydroxide, generally in the presence of a small amount of water at temperatures in the range of about 50°–150° C.

Phosphorus sulfides useful in preparing the dithiophosphoric acids of this invention include such phosphorus sulfides as $P_2S_5$, $P_5S_7$, $P_4S_8$, etc. However, for reasons of low cost reactivity and availability, phosphorus pentasulfide ($P_2S_5$) is preferred.

Hydrocarbyl hydroxy compounds useful in preparing the dihydrocarbyl dithiophosphoric acids of this invention include organic hydroxy compounds having from about 3 to about 50, preferably about 3 to 16 carbon atoms. Hydroxy compounds such as aliphatic, aromatic and unsaturated alcohols can be used. Examples of aliphatic alcohols useful in the invention include n-propanol, isopropanol, isobutanol, methylisobutylcarbanol, isodecanol, isooctanol, amyl alcohol, n-butanol, t-butanol, n-hexanol, 2-ethylhexanol, n-decanol, t-dodecanol, n-hexadecanol, and mixtures thereof. Useful alcohols include mixed "OXO" aliphatic alcohols including the $C_{4-16}$ alcohols obtained by the reaction of olefins with carbon monoxide followed by the hydrogenation of the resulting aldehydes. Aromatic hydroxy compounds such as phenols, substituted phenols, disubstituted phenols, substituted naphthol, etc. can be used to prepare zinc salts having substantially improved thermal stability in contrast to aliphatic alcohols. However, dihydrocarbyl dithiophosphoric acid compounds prepared from aromatic hydroxy compounds can react more slowly with basically reacting zinc compounds. The above aliphatic and aromatic hydroxy compounds can contain a variety of well known functional substituent groups such as polyether groups, halogen groups, acyloxy groups, etc. However, the hydrocarbon solubility of the resulting dithiophosphoric acids cannot be substantially reduced by the substitutent groups. Preferred dithiophosphoric acids having optimal performance can be obtained from isopropyl alcohol, methylisobutylcarbanol, amyl alcohol, isodecyl alcohol, isopropyl alcohol, isooctyl alcohol, nonyl phenol, and mixtures thereof.

In somewhat greater detail, the zinc additives of this invention are commonly prepared by slurrying phosphorus pentasulfide in inert hydrocarbon solvent and adding the hydrocarbyl hydroxy compound to the phosphorus pentasulfide slurry. The phosphorus pentasulfide slurry can be reacted with about 4 moles (3–5 moles) of hydroxy compound or mixtures thereof per mole of phosphorus sulfide compound. Preferably, an amount of phosphorus pentasulfide is used such that little unreacted phosphorus sulfide compound remains after the reaction. Accordingly, a slight molar access of hydroxy compound, about 4.1–4.5 moles of hydroxy compound per mole of phosphorus sulfide can be used. To avoid decomposition of the reactants and the reaction products, the reaction can be performed at a temperature from about 30°–250° C. under an inert atmosphere. Preferably, the reaction is conducted at about 100°–150° C. Depending on purity, concentration and temperature, the reaction can be completed in about 30 minutes to 12 hours. However, commonly the reaction is complete in 3–5 hours. The end of the reaction can conveniently be determined by monitoring the specific gravity of the reaction mixture, or hydrogen sulfide generation. The reaction product can then be stripped of excess volatiles including alcohols with an inert gas such as nitrogen. Unreacted phosphorus sulfide and other solids can conveniently be removed at this step by centrifugation or filtering.

The dihydrocarbyl dithiophosphoric acid is then contacted with an excess of zinc compound, preferably zinc oxide or zinc hydroxide, to produce the zinc salt. In order to promote complete neutralization and to reduce consumption of zinc compounds, about 1.05–1.50 moles, preferably 1.05–1.25 moles, of zinc compound is contacted with the dihydrocarbyl dithiophosphoric acid. The reaction is commonly performed at a temperature between 30°–250° C., preferably at a temperature of about 100° C., to prevent substantial thermal decomposition of substituents. The reaction can be continued for a period of up to about 10 hours depending on concentration of reactants, purity and reaction temperature to insure completion. Water is removed by stripping the reaction mixture with an inert gas stream. The product can be filtered or centrifuged to remove residual solids.

The ammonia compound can be added to the reaction mixture at any stage prior to or subsequent to the complete addition of the zinc compound with the acid compound. The ammonia compound can be added at any stage of the neutralization reaction up to removal of excess zinc compound from the reaction mass. The ammonia compound can be added commonly in catalytic amounts comprising from about 0.001–0.5 moles, preferably about 0.001 to 0.2, most preferably about 0.001 to about 0.1 moles of ammonia per mole of dihydrocarbyl dithiophosphoric acid. The ammonia compound can be added neat or in combination with any of the reactants or in combination with the inert diluents present in the reaction mixture.

The above reactions for the preparation of the additives of this invention can be prepared in batch or continuous processes. In batch processes, the solution of reactant or reactants may be added to the other reactants in a suitable vessel. After the reaction the products are removed to appropriate purification equipment. In continuous processes, two or more components in solution or solvent can be charged to different (countercurrent processes) or the same reaction zone, e.g., the upper end of a vertical zone maintained at a suitable elevated temperature. The product can commonly be withdrawn from the other end into appropriate purification strippers or filters.

The reactions producing the additives of this invention can be carried out in a solvent substantially inert to the reactants and products. The reaction can be preferably carried out in lubricating oil since the products of the reaction will ultimately be dissolved in lubricating oil compositions. However, other useful solvents include paraffins, chlorinated paraffins, ethers, aromatic solvents and others. Other preferred solvents include hexane, heptane, diethylether, petroleum ether, toluene, benzene, xylene, etc.

The additive compositions of this invention are useful in such lubricating oils as synthetic, animal, vegetable or mineral oils. Ordinary mineral lubricating oils are preferred by reason of their availability, general excellence and low cost. However, for certain applications, other oils may be preferred. Normally, the lubricant oils are fluid and have a viscosity greater than about 4.0 Saybolt Universal Seconds at 210° F., preferably greater than 40 Saybolt Universal Seconds at 410° F.

This invention also contemplates the presence of other additives and lubricating compositions. Such additives include, for example, pour point depressants, antifoam agents, extreme pressure agents, rust inhibiting agents, oxidation and corrosion inhibitors, including Mannich or succinic type dispersants, Group II metal sulfonates, Group II metal phenates, etc. Depending on the nature of the oil in the intended environment, different amounts of the zinc additive composition can be needed in order to be effective. Generally, about 0.01 to 10 weight percent or more, commonly to conserve additive, preferably from about 0.2 to about 5 weight percent of the additive is useful in the oil as an effective wear, corrosion and oxidation resistant amount.

The following examples are illustrative of the preparation of the additives of this invention.

EXAMPLE I

Into a one-liter, 3-neck flask equipped with a gas inlet tube, dropping funnel, stirrer, reflux condenser, temperature controller and heater was charged 49 gm (0.6 mole) of zinc oxide, and 78 gms of finished zinc dihydrocarbyl dithiophosphate additive essentially similar to that prepared in this Example. The mixture was stirred and heated to about 100° F. (38° C.). Into the flask was charged dropwise 350 gm (1.1 moles) of the dihydrocarbyl dithiophosphoric acid of Example XVIII at a rate to keep the temperature below about 170° F. (77° C.). When the addition of the acid was complete, 1.0 milliliters (0.018 mole) of 30 vol. % aqueous ammonia was added to the mixture. The mixture was allowed to react for about 15 minutes and was then stripped and filtered.

EXAMPLE II

Example I was repeated except 56 gms (0.69 mole) of zinc oxide was used in place of the 49 gms of zinc oxide.

EXAMPLE III

Example I was repeated except with 2.0 milliliters (0.036 mole) of 30 vol. % aqueous ammonia in place of the 1.0 milliliters of ammonia.

EXAMPLE IV

Example II was repeated except with 2.0 milliliters (0.036 mole) of 30 vol. % aqueous ammonia, in place of the 1.0 milliliters of ammonia, and 56 gms (0.69 mole) zinc oxide in place of the 49 gms of zinc oxide.

EXAMPLE V

Example II was repeated except that the ammonium hydroxide was omitted.

EXAMPLE VI

Example II was repeated except the reaction was performed at a temperature of 205° F. instead of 170° F.

EXAMPLE VII

Example I was repeated except that the reaction was performed at a temperature of 205° F. instead of 170° F.

EXAMPLE VIII

Example III was repeated except that the reaction was performed at a temperature of 205° F. instead of 170° F.

EXAMPLE IX

Example VIII was repeated with identical reaction conditions.

EXAMPLE X

Example V was repeated except with the dialkyldithiophosphoric acid product of Example XIX.

EXAMPLE XI

Example II was repeated except with the dihydrocarbyldithiophosphoric acid product of Example XIX.

EXAMPLE XII

Example XI was repeated except with a 5 min. reaction time instead of 15 minutes.

EXAMPLE XIII

Example I was repeated except with the dihydrocarbyldithiophosphoric acid of Example XIX.

EXAMPLE XIV

Example X was repeated except that the reaction was performed at 205° F. instead of 170° F.

EXAMPLE XV

Example VI was repeated except with a reaction time of 15 min. instead of 10 min., and with the dihydrocarbyldithiophosphoric acid of Example XIX.

EXAMPLE XVI

Example XV was repeated except with a 5 minute reaction time instead of 15 minutes.

EXAMPLE XVII

Example VII was repeated except with the dihydrocarbyldithiophosphoric acid of Example XIX.

EXAMPLE XVIII

Into a three-liter, 3-neck flask equipped with a gas inlet tube, dropping funnel, stirrer, reflux condenser, stirrer, temperature controller and heater was charged 656 gms (2.95 moles) of Stauffer $P_2S_5$, and 350 ml SX-5 oil. The mixture was stirred and 988 gms of an alcohol mixture comprising 65 mole % isobutanol, 25 mole % n-amyl alcohol, and 10 mole % n-octanol alcohol was added to the mixture dropwise at a rate such that the temperature did not exceed about 100° C. At the end of the addition of the alcohols, the reaction mixture was stripped of volatile material and was filtered of particulate matter.

EXAMPLE XIX

Example XVIII was repeated with Monsanto $P_2S_5$.

EXAMPLE XX

Into a three-liter, 3-neck flask equipped with a gas inlet tube, dropping funnel, stirrer, reflux condenser, stirrer, temperature controller and heater was charged 666 gms (3.00 moles) of $P_2S_5$, and 350 ml SX-5 oil. The mixture was stirred and 972 gms (12.0 moles) of a mixture of 50 mole % isopropanol and 50 mole % methyl isobutyl carbinol was added to the mixture dropwise at a temperature that did not exceed about 100° C. At the end of the addition of the alcohols, the reaction mixture was stripped of volatile material and was filtered of particulate matter.

Into a one-liter, 3-neck flask equipped with a gas inlet tube, dropping funnel, stirrer, reflux condenser, temperature controller and heater was charged 47 gm (0.58 mole) of zinc oxide which was stirred and heated to about 100° F. (38° C.). Into the flask was charged dropwise 350 gm (1.1 moles) of the dihydrocarbyl dithiophosphoric acid prepared above at a rate to keep the temperature below about 170° F. (77° C.). When the addition of the acid was complete, 0.23 gm (0.014 mole) of 30 aqueous ammonia was added to the mixture. The mixture was allowed to react for about 15 minutes and was then stripped and filtered. The pH of the finished product was 6.15.

EXAMPLE XXI

Example XX was repeated and the pH was 6.1.

EXAMPLE XXII

Example XX was repeated without the ammonia addition and the pH was 5.5.

EXAMPLE XXIII

Example XXI was repeated without the ammonia addition and the pH was 5.5.

TABLE I

EFFECT OF ZINC EXCESS, AMMONIA AND REACTION TEMPERATURE ON PRODUCT pH

| PRODUCT OF EXAMPLE | TEMP (°F.) | ZnO (MOLE %) | RESIDENCE TIME (MIN.) | NH4OH (ML) | pH BEFORE STRIPPING | pH AFTER STRIPPING |
|---|---|---|---|---|---|---|
| V | 170 | 25 | 15 | 0 | 5.9 | 4.6 |
| II | 170 | 25 | 15 | 1 | 6.25 | 5.6 |
| IV | 170 | 25 | 15 | 2 | 7.4 | 7.1 |
| III | 170 | 10 | 15 | 2 | 7.25 | 6.85 |
| VI | 205 | 25 | 10 | 1 | 6.1 | 5.9 |
| VII | 205 | 10 | 15 | 1 | 5.9 | 5.6 |
| VIII | 205 | 10 | 15 | 2 | 6.1 | 5.9 |
| IX | 205 | 10 | 10 | 2 | 6.2 | 6.0 |
| X | 170 | 25 | 15 | 0 | 5.9 | 5.7 |
| XI | 170 | 25 | 15 | 1 | 6.2 | 6.1 |
| XII | 170 | 25 | 5 | 1 | 6.3 | 5.95 |
| XIII | 170 | 10 | 15 | 1 | 6.2 | 5.65 |
| XIV | 205 | 25 | 15 | 0 | 6.0 | 5.95 |
| XV | 205 | 25 | 15 | 1 | 6.3 | 6.2 |
| XVI | 205 | 25 | 5 | 1 | 6.3 | 6.1 |
| XVII | 205 | 10 | 15 | 1 | 6.15 | 6.0 |

The pH measurements on the products of this invention can be performed by placing a 1.5 gm sample of the product in a 150 milliliter beaker and adding 100 milliliters of a test solution prepared by mixing 1472 milliliters of isopropanol, 1472 milliliters of toluene and 256 milliliters of distilled water. The resulting mixture is stirred until the sample is dissolved. The pH of the mixture is measured using a standarized pH meter.

We have observed in engine tests, such as the CRC L-38 engine test, which evaluate the effects of lubricants on corrosion of metal surfaces in engines such as bearing material, that lubricants containing zinc dihydrocarbyl dithiophosphate compositions having a pH less than 6, as measured in the above procedure, will fail in the engine test due to excessive corrosion. If a bearing material loses greater than about 40 milligrams of weight due to corrosion, the lubricant is said to have failed the engine test. Zinc additives having a pH of about 6.1-6.8 will pass the engine test with a bearing corrosion weight loss of about 30 milligrams or less.

An examination of the data in Table I and Examples XV through XXIII, shows that the addition of catalytic amount of ammonia can substantially increase the pH of the reaction product. At both 170° F. and 205° F. reaction temperature, a product with a pH greater than about 6 can be produced at a variety of reaction times and a variety of molar excesses of zinc oxide. Clearly, more stable products result from the use of catalytic amounts of ammonia.

The foregoing examples of tables of data are illustrative of the invention, and should not be used to unduly limit the scope of the invention. The invention resides wholly within the claims hereinafter appended.

We claim:

1. An improved process for the preparation of a zinc dihydrocarbyl dithiophosphate composition that provides lubricants with resistance to corrosion, wear and oxidation, which comprises reacting a dihydrocarbyl dithiophosphoric acid, a zinc compound and an effective neutralization reaction catalytic amount of ammonia or an ammonia-yielding compound.

2. The process of claim 1 wherein the ammonia-yielding compound comprises ammonium hydroxide.

3. The process of claim 1 wherein the ammonia-yielding compound comprises an ammonium hydrocarbyl sulfonate.

4. The process of claim 1 wherein the zinc compound comprises zinc oxide.

5. The process of claim 1 wherein the zinc compound comprises zinc hydroxide.

6. The process of claim 1 wherein the dihydrocarbyl dithiophosphoric acid comprises the reaction product of a hydrocarbyl hydroxy compound and a phosphorus sulfide.

7. The process of claim 6 wherein the hydrocarbyl hydroxy compound comprises an aliphatic alcohol having from about 3 to about 16 carbon atoms.

8. The process of claim 6 wherein the hydrocarbyl hydroxy compound comprises a mixture of aliphatic alcohols having about 3 to 16 carbon atoms.

9. The process of claim 8 wherein the aliphatic alcohols are selected from the group consisting of isopropanol, isobutanol, methylisobutylcarbanol, isodecanol, isooctanol, and amyl alcohol.

10. The process of claim 1 wherein the ammonia or the ammonia-yielding compound is present at a concentration of about 0.001 to about 0.5 moles of ammonia or the ammonia-yielding compound per mole of the dihydrocarbyl dithiophosphoric acid.

11. The process of claim 1 wherein the ammonia or the ammonia-yielding compound is present at a concentration of 0.001–0.2 moles of ammonia or the ammonia-yielding compound per mole of the dihydrocarbyl dithiophosphoric acid.

12. The process of claim 1 wherein the ammonia or the ammonia-yielding compound is present at a concentration of 0.001–0.1 moles of ammonia or the ammonia-yielding compound per mole of dihydrocarbyl dithiophosphoric acid.

13. The process of claim 1 wherein the pH of the composition is greater than about 6.

* * * * *